United States Patent
Uchimura et al.

(10) Patent No.: US 7,605,271 B2
(45) Date of Patent: Oct. 20, 2009

(54) SUPERHIGH PURITY IONIC LIQUID

(75) Inventors: Hirofumi Uchimura, Kyoto (JP); Manabu Kikuta, Kyotanabe (JP)

(73) Assignee: Dai-Ichi Kogyo Seiyaku Co., Ltd, Kyoto-Shi, Kyoto (JP)

( * ) Notice: Subject to any disclaimer, the term of this patent is extended or adjusted under 35 U.S.C. 154(b) by 207 days.

(21) Appl. No.: 11/356,799

(22) Filed: Feb. 17, 2006

(65) Prior Publication Data

US 2006/0223995 A1    Oct. 5, 2006

(30) Foreign Application Priority Data

Mar. 29, 2005    (JP)    ............... 2005-096423

(51) Int. Cl.
*C07D 233/02* (2006.01)
(52) U.S. Cl. .................................. 548/300.1
(58) Field of Classification Search ............... 548/300.1
See application file for complete search history.

(56) References Cited

U.S. PATENT DOCUMENTS

2006/0063945 A1    3/2006    Wasserscheid et al.

FOREIGN PATENT DOCUMENTS

| EP | 1182196 | 2/2002 |
| EP | 1182196 A1 * | 2/2002 |
| JP | 9-509888 | 10/1997 |
| WO | WO-96/18459 | 6/1996 |
| WO | WO 2004080974 A1 * | 9/2004 |
| WO | WO-2004/096776 | 11/2004 |
| WO | WO-2005/021484 | 3/2005 |

OTHER PUBLICATIONS

Feb. 1, 2004 Creation of Function and Application of Ionic Liquid Green Chemistry Series vol. 2 pp. 31-32.
1992 "Air and Water Stable 1-Ethyl-3-methylimidazolium Based Ionic Liquids" John S. Wilkes et al. Chemical Communication of Journal of Chemical Society Section 965 pp. 965-967.
Jan. 1, 1992 "Air and Water Stable 1-Ethyl-3-methylimidazolium Based Ionic Liquids" John S. Wilkes et al. J. Chem. Soc., Chem. Commun. pp. 965-967.

* cited by examiner

*Primary Examiner*—Peter G O'Sullivan
*Assistant Examiner*—Sudhakar Katakam
(74) *Attorney, Agent, or Firm*—Jordan and Hamburg LLP

(57) ABSTRACT

Provided is an ionic liquid, represented by the formula $K^+A^-$, having a very low content of impurities, especially a low content of halogen ions and/or a low content of alkali metal, wherein $K^+$ is a quaternary ammonium ion, for example an imidazolium ion. Also provided is a quaternarization process for making the ionic liquid in reacted with an acid ester such as a sulfate or phosphate.

2 Claims, No Drawings

SUPERHIGH PURITY IONIC LIQUID

BACKGROUND OF THE INVENTION

1. Field of the Invention

The present invention concerns a halogen free ionic liquid at high purity which is applicable to electrochemical devices.

2. Description of the Related Art

Since an ionic liquid is less volatile, it can not be purified by distillation. Accordingly, purification at high degree of the ionic liquid is one of important subjects.

An existent ionic liquid is synthesized by synthesizing a cationic onium salt by quarternization using an alkyl halide and then conducting salt-exchange thereof by using an acid (HA) or a salt (MA) as an anion.

Since the ionic liquid synthesized by the method described above is formed by way of the cationic onium salt having a halogen ion as a counter ion, it involves a problem that halogen ions remain also after conversion to an aimed ionic liquid. Particularly, a completely halogen free ionic liquid has been demanded in the application use of device materials that suffer from significant effects by the incorporation, particularly, of halogen ions.

As a method of removing the halogen ions, there is generally a method of evaporizing them as hydrogen halide by using an acid (HA), but the method involves a problem of evolving corrosive and deleterious gases. Further, as reported in "Creation of Function and Application of Ionic Liquid", Green Chemistry Series vol. 2, published from NTS in Feb. 1, 2004, p. 31 to 32, a method of converting the halogen ions into an alkali metal salt (MX) by using an alkali metal salt (MA) of an anion and removing the same by water washing has also been used frequently, but it is difficult by the method to remove starting materials and organic halogenated products derived therefrom. As other method of removing halogens, there are reported a method of removing halogen ions as an insoluble silver halide by using silver acetate or the like in Chemical Communication of Journal of Chemical Society, section 965 in 1992, and a method of removing halogen ions by converting them into an insoluble lead halide by using a lead salt in JP-A-9-509888, but since metal salts used for the methods are expensive and wastes containing deleterious metals are formed, they are far from inexpensive and easy synthesizing methods.

SUMMARY OF THE INVENTION

As described above, in the existent production of the ionic liquid using an alkyl halide as a quarternizing agent, since it is by way of a cationic onium salt with halogen ions being as the counter ions, halogen ions are evaporated as deleterious gases, or they should be removed by using expensive reagents, and it has been difficult to render the liquid completely halogen free. Then, in a case of applying such ionic liquids to electrochemical devices, for example, electric cells or capacitors, this gives rise to a problem of causing corrosion of electrodes and so on by halogen ions.

In view of the foregoing problems, the present invention intends to provide an ionic liquid with extremely less impurity content such as of halogen ions, obtainable easily at a relatively reduced cost and usable suitably as an electrolyte for use in various kinds of electrochemical devices including electric cells and capacitors, reaction solvents and so on.

An ionic liquid of the invention is an ionic liquid represented by the following general formula (1) comprising a pair of cation $K^+$ and an anion $A^-$ in which the content of an alkali metal as an impurity is 5 ppm or less and the content of a halogen ion is 1 ppm or less.

$$K^+A^- \qquad (1)$$

The cation described above is preferably one or more of members selected from the group represented by the following general formula (2):

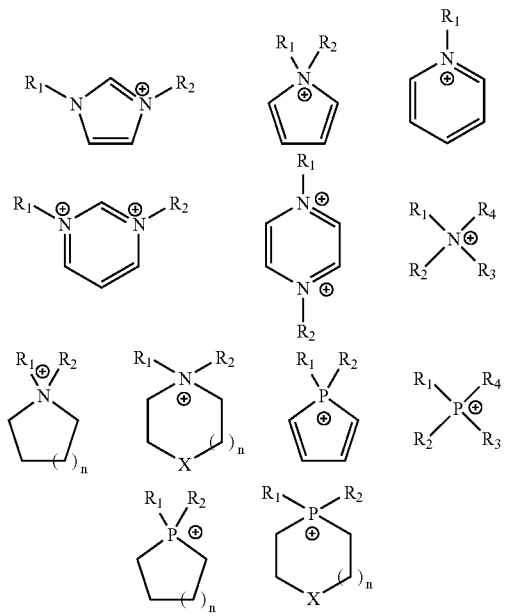

$R_1$ to $R_4$ in the formula (2) each independently represents a linear or branched alkyl group of 1 to 8 carbon atoms, and may include one set or more of identical groups, and X represents a hetero atom such as oxygen, sulfur, etc.

The cation described above can be obtained by quarternizing a tertiary amine compound or a tertiary phosphine compound by using an acid ester represented by the following general formula (3) and then conducting salt exchange.

ROY (3)

$$OY: \; O-\overset{\overset{\displaystyle O}{\|}}{\underset{\underset{\displaystyle O}{\|}}{S}}-OR, \quad O-\overset{\overset{\displaystyle O}{\|}}{S}-OR, \quad O-\overset{\overset{\displaystyle O}{\|}}{\underset{\underset{\displaystyle OR}{|}}{P}}-OR,$$

$$O-\overset{}{\underset{\underset{\displaystyle OR}{|}}{P}}-OR, \quad O-\overset{\overset{\displaystyle O}{\|}}{C}-OR, \quad O-\overset{\overset{\displaystyle O}{\|}}{\underset{\underset{\displaystyle O}{\|}}{S}}-R,$$

$$O-\overset{\overset{\displaystyle O}{\|}}{\underset{\underset{\displaystyle O}{\|}}{S}}-R, \quad O-\overset{}{\underset{\underset{\displaystyle OR}{|}}{P}}-R, \quad O-\overset{\overset{\displaystyle O}{\|}}{\underset{\underset{\displaystyle R}{|}}{P}}-R, \quad O-\overset{\overset{\displaystyle O}{\|}}{C}-R$$

R in the general formula (3) is a linear or branched alkyl group of 1 to 8 carbon atoms and a plurality of R contained in one compound may be identical or different with each other.

According to the invention, since the content of the impurity typically represented by the halogen ion is extremely low, a high purity ionic liquid used suitably to various kinds of electrochemical devices can be provided.

The halogen free ionic liquid at high purity of the invention can be obtained easily at a reduced cost by quarternizing various kinds of tertiary amines or tertiary phosphine compounds using an acid ester which is inexpensive and suitable also to industrial use and conducting salt exchange with an aimed anion.

PREFERRED EMBODIMENTS OF THE INVENTION

The cation $K^+$ applied to the compound represented by the general formula (1) is not particularly limited and includes, for example, imidazolium cation, pyrrolium cation, pyrizinium cation, pyrimidinium cation, pyrazinium cation, ammonium cation, pyrrolidinium cation, piperidinium cation, phospholium cation, phosphonium cation, phosphorolium cation, and also includes those containing hetero atoms, for example, oxygen or sulfur, such as morpholine or thiomolpholine.

They include, more specifically, 1,3-dimethyl imidazolium, 1-methyl-3-ethyl imidazolium, 1-methyl-3-propyl imidazolium, 1-methyl-3-hexyl imidazolium, 1-methyl-3-octyl imidazolium, 1,3-diethyl imidazolium, 1-ethyl-3-propyl imidazolium, 1-ethyl-3-hexyl imidazolium, 1-ethyl-3-octyl imidazolium, 1,3-dipropyl imidazolium, 1-hexyl-3-propyl imidazolium, 1-propyl-3-octyl imidazolium, 1,1-dimethyl pyrrolium 1-ethyl-1-methyl pyrrolium, 1-methyl-1-propyl pyrrolium, 1-hexyl-1-methyl pyrrolium, 1-methyl-1-octyl-pyrrolium, 1,1-diethyl pyrrolium, 1-ethyl-1-propyl pyrrolium, 1-ethyl-1-hexyl pyrrolium, 1-ethyl-1-octyl pyrrolium, 1,1-dipropyl pyrrolium, 1-propyl-1-hexyl pyrrolium, 1-octyl-1-propyl pyrrolium, 1-methyl-1-pentyl pyrrolium, 1-ethyl-1-pentyl pyrrolium, 1,1-dipentyl pyrrolium, 1,1-dihexyl pyrrolium, 1-hexyl-1-octyl pyrrolium, 1-methyl pyrizinium, 1-ethyl pyrizinium, 1-propyl pyrizinium, 1-pentyl pyrizinium, 1-hexyl pyrizinium, 1-octyl pyrizinium, 1,3-dimethyl pyrimidinium, 1-ethyl-3-methyl pyrimidinium, 1-methyl-3-propyl pyrimidinium, 1-methyl-3-hexyl pyrimidinium, 1-methyl-3-octyl pyrimidinium, 1,3-diethyl pyrimidinium, 1-ethyl-3-propyl pyrimidinium, 1-ethyl-3-hexyl pyrimidinium, 1-ethyl-3-octyl pyrimidinium, 1,3-dipropyl pyrimidinium, 1-hexyl-3-propyl pyrimidinium, 1-octyl-3-propyl pyrimidinium, 1,3-dihexyl pyrimidinium, 1-hexyl-3-octyl pyrimidinium, 1,3-dioctyl pyrimidinium, 1,4-dimethyl pyrazinium, 1-ethyl-4-methyl pyrazinium, 1-methyl-4-propyl pyrazinium, 1-methyl-4-hexyl pyrazinium, 1-methyl-4-octyl pyrazinium, 1,4-diethyl pyrazinium, 1-ethyl-4-propyl pyrazinium, 1-ethyl-4-hexyl pyrazinium, 1-ethyl-4-octyl pyrazinium, 1,4-dipropyl pyrazinium, 1-hexyl-4-propyl pyrazinium, 1-octyl-4-propyl pyrazinium, 1,4-dihexyl pyrazinium, 1-hexyl-4-octyl pyrazinium, 1,4-dioctyl pyrazinium, hexyl trimethyl ammonium, diethyl dimethyl propyl ammonium, diethyl methyl propyl ammonium, octyl diethyl methyl ammonium, 1,1-dimethyl pyrrolidinium, 1-ethyl-1-methyl pyrrolidinium, 1,1-diethyl pyrrolidinium, 1-methyl-1-propyl pyrrolidinium, 1-methyl-1-hexyl pyrrolidinium, 1-methyl-1-octyl pyrrolidinium, 1-ethyl-1-propyl pyrrolidinium, 1,1-dipropyl pyrrolidinium, 1-ethyl-1-hexyl pyrrolidinium, 1-ethyl-1-octyl pyrrolidinium, 1-hexyl-1-propyl pyrrolidinium, 1-octyl-1-propyl pyrrolidinium, 1,1-dihexyl pyrrolidinium, 1-hexyl-1-octyl pyrrolidinium, 1,1-dioctyl pyrrolidinium, 1,1-dimethyl piperidinium, 1-ethyl-1-methyl piperidinium, 1,1-diethyl piperidinium, 1-methyl-1-propyl piperidinium, 1-methyl-1-hexyl piperidinium, 1-methyl-1-octyl piperidinium, 1-ethyl-1-propyl piperidinium, 1,1-dipropyl piperidinium, 1-ethyl-1-hexyl piperidinium, 1-ethyl-1-octyl piperidinium, 1-hexyl-1-propyl piperidinium, 1-octyl-1-propyl piperidinium, 1,1-dihexyl piperidinium, 1-hexyl-1-octyl piperidinium, 1,1-dioctyl piperidinium, hexyl trimethyl phosphonium, octyl trimethyl phosphonium, hexyl diethyl methyl phosphonium, octyl diethyl methyl phosphonium, diethyl dimethyl propyl phosphonium, 4-methyl-4-ethyl morpholine, 4-methyl-4-propyl morpholine, 4-ethyl-4-hexyl morpholine, 4-methyl-4-ethyl thiomorpholine, 4-methyl-4-propyl thiomorpholine, and 4-ethyl-4-hexyl thiomorpholine.

Also the anion $A^-$ applied to the compound represented by the general formula (1) is not particularly limited and includes, for example, inorganic fluoric anions such as tetrafluoro borate and hexafluoro phosphate, alkane sulfonate anions represented by $RSO_3^-$ (where R represents an alkyl group or fluoro alkyl group), alkane sulfonyl imide anions represented by $(RSO_2)_2N^-$ (where R represents an alkyl group or a fluoro alkyl group), a halogenated sulfonyl imide anions represented by $(XSO_2)_2N^-$ (where X represents a halogen), alkane sulfonyl carbo anions represented by $(RSO_2)_3C^-$ (where R represents an alkyl group or fluoro alkyl group), and organic carboxylic acids represented by $RCOO^-$ (where R represents an alkyl group or fluoro alkyl group).

In the invention, the cation represented by the general formula (2) is synthesized by using the acid ester as described above. The acid ester is a compound represented by the general formula (3) and specifically includes, for example, esters of inorganic acids such as sulfuric acid, sulfurous acid, phosphoric acid, phosphorous acid, and carbonic acid, and esters of organic acid such as sulfonic acid, phosphonic acid, and carboxylic acid.

In the general formula (3), R represents a linear or branched alkyl group of 1 to 8 carbon atoms. Examples of the alkyl group represented by R include linear or branched alkyl groups of 1 to 8 carbon atoms such as methyl group, ethyl group, n-propyl group, i-propyl group, n-butyl group, sec-butyl group, tert-butyl group, pentyl group, hexyl group, heptyl group, and octyl group, and preferred examples include linear or branched alkyl groups of 1 to 4 carbon atoms such as methyl group, ethyl group, propyl group, and butyl group.

In the method of synthesizing the cation used in the invention, the acid ester can be used by from 1 to 10 equivalent amount, preferably, from 1 to 3 equivalent amount based on one mol of the tertiary amine or the tertiary phosphine compound. Since violent heat generation may sometimes occur upon introduction of the acid ester, it is preferably dropped slowly taking one hour or more. An aimed product can be obtained at a high yield by reacting at a temperature usually from 0° C. to 200° C., preferably, from 20° C. to 120° C. as the reaction temperature for 1 to 100 hours.

The reaction solvent may not always be used but it is preferred to use the solvent. The reaction solvent includes alcohol solvents such as methanol, ethanol, propanol, ethylene glycol and so on, ester solvents such as methyl acetate, ethyl acetate, propyl acetate, γ-butyrolactone, propione carbonate and so on, nitrile solvents such as acetonitrile, propionitrile and so on, aromatic solvents such as benzene, toluene, xylene and so on, and N,N-dimethylformamide, and dimethylsulfoxide, and they are used each alone or as an optional mixture of two or more of them.

The thus obtained cationic onium salt can be easily subjected to salt exchange at a room temperature by mixing with an equimolar amount of an anionic alkali metal salt in water or a solvent. The solvent used is not particularly limited and water, nitrile solvents such as acetonitrile or alcohol solvents such as methanol and ethanol are preferred, and they are used each alone or as an optional mixture of two or more them. In a case where the aimed ionic liquid is hydrophobic, water is most preferred. An ionic liquid with an alkali metal content of 5 ppm or less and a halogen ion content of 1 ppm or less can be obtained by recovering an ionic liquid layer separated after the reaction, adding ion exchanged water of 30 wt % or more and conducting water washing and liquid separation by once or more, preferably, repeating five times or more. Further, in a case of using an organic solvent as the reaction solvent, salts as by-products may sometimes be deposited. An ionic liquid with an alkali metal content of 5 ppm or less and an halogen ion content of 1 ppm or less can be obtained by adding 30 wt % or more of ion exchanged water after filtering the precipitated salts and concentrating the liquid filtrates, and conducting water washing and liquid separation once or more, preferably repeating five times or more, and depending on the case, adding 30 wt % or more of ion exchanged water in the same manner after extracting to a hydrophobic organic solvent and conducting water washing and liquid separation once or more, preferably repeating five times or more.

The ionic liquid of the invention is used suitably as an electrolyte salt for use in electrochemical devices or electrolytes for use in electrochemical devices. In this case, an organic solvent can also be used optionally in combination.

EXAMPLE

Examples of the invention are to be described below but the invention is not restricted to them.

(1) Synthesis of 1-ethyl-3-methyl imidazolium.bis(trifluoro methane sulfonyl)imide (compound represented by the following formula)

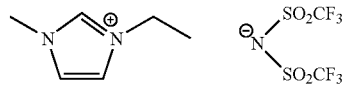

Example 1

To a 200 ml four necked flask equipped with a stirrer, a dropping funnel, a cooling tube and a thermometer, 32.84 g (0.4 mol) of 1-methyl imidazole and 40 ml of toluene were charged and heated at 40° C., to which 67.84 g (0.44 mol) of diethyl sulfuric acid was dropped slowly for one hour. The temperature was elevated from 40° C. to 55° C. in this case. After dropping and further reacting at 40° C. for 2 hours, unreacted diethyl sulfuric acid was removed by solvent cleaning with toluene. Then, 94.3 g of 1-ethyl-3-methyl imidazolium.ethyl sulfate salt was obtained by drying under a reduced pressure.

Then, 23.63 g of the obtained 1-ethyl-3-methyl imidazolium.ethyl sulfate salt was dissolved in 10 ml of water, and a solution in which 28.71 g of lithium (bis trifluoromethane sulfonyl) imide was dissolved in 10 ml of water was added thereto at a room temperature and stirred. From separated two layers, the lower layer was fractionated and by-products were removed by adding 40 wt % of purified water and water washing five times, and vacuum drying was applied to obtain 34.37 g of 1-ethyl-3-methyl imidazolium (bistrifluoromethane sulfonyl) imide. When the contents of the alkali metal ions and halogen ions were examined by ICP emission spectrochemical analysis (hereinafter simply referred to as "ICP analysis"), the total alkali metals was 1.3 ppm or less, chloride ion was 0.2 ppm, and each of iodide and bromide ions was 0.1 ppm or less (lower than ICP detection limit).

Comparative Example 1

To a 200 ml four necked flask equipped with a stirrer, a dropping funnel, a cooling tube and a thermometer, 32.84 g (0.4 mol) of 1-methyl imidazole and 40 ml of toluene were charged and heated at 50° C., to which 68.63 g (0.44 mol) of ethyl iodide was dropped slowly taking one hour. After dropping, and further reacting at 50° C. for 4 hours, deposited solids were filtered, subjected to solvent cleaning and dried under a reduced pressure to obtain 90.47 g of 1-ethyl-3-methyl imidazolium iodide salt.

Then, 90.47 g of the obtained 1-ethyl-3-methyl imidazolium.iodide salt was dissolved in 10 ml of water, and a solution in which 28.71 g of lithium (bis trifluoromethane sulfonyl) imide was dissolved in 10 ml of water was added thereto at a room temperature and stirred. From separated two layers, the lower layer was fractionated and by-products were removed by adding 40 wt % of purified water and water washing five times, and vacuum drying was applied to obtain 33.57 g of 1-ethyl-3-methyl imidazolium (bistrifluoromethane sulfonyl) imide. As a result of ICP analysis, 2.8 ppm of the total alkali metals, 3.2 ppm of chlorine, and 4.8 ppm of iodine were contained.

(2) Synthesis of 1-methyl-3-propyl imidazolium.bis(trifluoro ethane sulfonyl)imide (compound represented by the following formula)

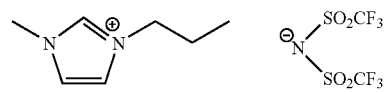

Example 2

To a 50 ml four necked flask equipped with a stirrer, a dropping funnel, a cooling tube and a thermometer, 41.05 g (0.5 mol) of 1-methyl imidazole and 50 ml of toluene were charged and, after heating at 80° C., 76.00 g (0.55 mol) of propyl methane sulfonate was dropped slowly taking one hour or more. They were stirred at a refluxing temperature for 40 hours. After cooling, solvent cleaning was conducted with toluene to obtain 99.13 g of 1-methyl-3-propyl-imidazolium methane sulfonate salt by drying under a reduced pressure. Then, 99.13 g of the obtained 1-ethyl-3-propyl imidazolium.methane sulfonate salt was dissolved in 80 ml of water, and a solution in which 139.24 g of lithium bis(trifluoromethane sulfonyl) imide was dissolved in 80 ml of water was added thereto at a room temperature and stirred. From separated two layers, the lower layer was fractionated and by-products were removed by adding 40 wt % of purified water and by water washing five times, and vacuum drying was applied to obtain 178.75 g of 1-methyl-3-propyl imidazolium bis(trifluoromethane sulfonyl) imide. As a result of ICP analysis, the total alkali metal was 2.1 ppm or less, the chloride ion was 0.6 ppm and each of iodide and bromide ions was 0.1 ppm or less (less than ICP detection limit).

Comparative Example 2

To a 50 ml four necked flask equipped with a stirrer, a dropping funnel, a cooling tube and a thermometer, 41.05 g (0.5 mol) of 1-methyl imidazole and 50 ml of toluene were charged, and heating at 50° C., 93.49 g (0.55 mol) of propyl iodide was dropped slowly taking one hour or more. After stirring under heating at 50° C. for 4 hours, precipitates were separated by filtration, washed by using toluene and dried under a reduced pressure to obtain 122.26 g of 1-methyl-3-propyl imidazolium iodide salt. Then, 122.26 g of the obtained 1-methyl-3-propyl imidazolium methane sulfonate salt was dissolved in 80 ml of water, and a solution in which 139.24 g of lithium bis(trifluoromethane sulfonyl)imide was dissolved in 80 ml of water was added thereto at a room temperature and stirred. From separated two layers, the lower layer was fractionated and by-products were removed by adding 40 wt % of purified water and by water washing five times and vacuum drying was applied to obtain 175.39 g of 1-methyl-3-propyl imidazolium bis(trifluoromethane sulfonyl) imide. As a result of ICP analysis, 2.4 ppm of total alkali metals, 2.9 ppm of chlorine and 6.5 ppm of iodine were contained.

(3) Synthesis of 1-methyl-3-hexyl imidazolium.bis(trifluoro methane sulfonyl)imide (compound represented by the following formula)

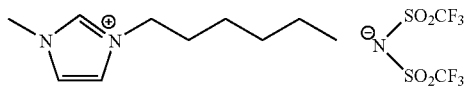

Example 3

To a 50 ml four necked flask equipped with a stirrer, a dropping funnel, cooling tube and a thermometer, 41.05 g (0.5 mol) of 1-methyl imidazole and 50 ml of toluene were charged and, after heating at 80° C., 146.52 g (0.55 mol) of dihexyl sulfonic acid was dropped slowly taking one hour or more. They were stirred at a refluxing temperature for 25 hours. After cooling, solvent cleaning was conducted with toluene to obtain 156.83 g of 1-methyl-3-hexyl-imidazolium hexyl sulfonate salt by drying under a reduced pressure. Then, 99.13 g of the obtained 1-methyl-3-hexyl imidazolium hexyl sulfonate salt was dissolved in 80 ml of water, and a solution in which 139.24 g of lithium bis(trifluoromethane sulfonyl) imide was dissolved in 80 ml of water was added thereto at a room temperature and stirred. From separated two layers, the lower layer was fractionated and by-products were removed by adding 40 wt % of purified water and by water washing five times, and vacuum drying was applied to obtain 197.31 g of 1-methyl-3-hexyl imidazolium bis(trifluoromethane sulfonyl) imide. As a result of ICP analysis, the total alkali metal was 2.7 ppm or less, the chloride ion was 0.7 ppm and each of iodide and bromide ions was 0.1 ppm or less (less than ICP detection limit).

Comparative Example 3

To a 50 ml four necked flask equipped with a stirrer, a dropping funnel, a cooling tube and a thermometer, 41.05 g (0.5 mol) of 1-methyl imidazole and 50 ml of toluene were charged and, after heating at 50° C., 90.24 g (0.55 mol) of hexyl bromide was dropped slowly taking one hour or more. They were stirred at a refluxing temperature for 5 hours. After cooling, precipitates were separated by filtration, subjected to solvent cleaning and dried under a reduced pressure to obtain 119.88 g of 1-methyl-3-hexyl imidazolium iodide salt. Then, 119.88 g of the obtained 1-methyl-3-hexyl imidazolium bromide salt was dissolved in 80 ml of water, to which 139.24 g of lithium bis(trifluoromethane sulfonyl)imide dissolved in 80 ml of water was added at a room temperature and stirred. From separated two layers, the lower layer was fractionated and by-products were removed by adding 40 wt % of purified water and by water washing five times and vacuum drying was applied to obtain 197.31 g of 1-methyl-3-hexyl imidazolium bis(trifluoromethane sulfonyl) imide. As a result of ICP analysis, 3.7 ppm of total alkali metals, 3.3 ppm of chlorine and 24 ppm of iodine were contained.

(4) Synthesis of 1-ethyl-3-methyl imidazolium bis(fluoro sulfonyl)imide

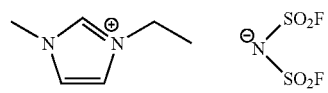

Example 4

To a 200 ml four necked flask equipped with a stirrer, a dropping funnel, a cooling tube and a thermometer, 32.84 g (0.4 mol) of 1-methyl imidazole and 40 ml of toluene were charged and heated at 30° C., to which 67.84 g (0.44 mol) of diethyl sulfuric acid was dropped slowly taking one hour. The temperature was elevated from 30° C. to 47° C. at this stage. After dropping and further reacting at 30° C. for 3 hours, unreacted diethyl sulfuric acid was removed by solvent cleaning with toluene. Then, 93.8 g of 1-ethyl-3-methyl imidazolium.ethyl sulfate salt was obtained by drying under a reduced pressure.

Then, 93.8 g of the obtained 1-ethyl-3-methyl imidazolium.ethyl sulfate salt was dissolved in 20 ml of water, and a solution in which 86.82 g of potassium bis(fluorosulfonyl) imide was dissolved in 20 ml of water was added thereto at a room temperature and stirred. From separated two layers, the lower layer was fractionated and by-products were removed by adding 40 wt % of purified water and water washing five times, and vacuum drying was applied to obtain 107.20 g of 1-ethyl-3-methyl imidazolium bis(fluorosulfonyl) imide. As a result of ICP analysis, the total alkali metals was 3.1 ppm or less, chloride ion was 0.3 ppm, and each of iodide and bromide ions was 0.1 ppm or less (lower than ICP detection limit).

Comparative Example 4

To a 200 ml four necked flask equipped with a stirrer, a dropping funnel, a cooling tube and a thermometer, 32.84 g (0.4 mol) of 1-methyl imidazole and 40 ml of toluene were charged and heated at 50° C., to which 68.63 g (0.44 mol) of ethyl iodide was dropped slowly taking one hour. After dropping and further reacting at 50° C. for 4 hours, precipitates were separated by filtration, subjected to solvent cleaning and dried under a reduced pressure to obtain 90.47 g of 1-ethyl-3-methyl imidazolium iodide salt.

Then, 90.47 g of the obtained 1-ethyl-3-methyl imidazolium iodide salt was dissolved in 20 ml of water, and a solution in which 86.82 g of potassium bis(fluorosulfonyl) imide was dissolved in 20 ml of water was added thereto at a room temperature and stirred. From separated two layers, the lower layer was fractionated and by-products were removed by adding 40 wt % of purified water and by water washing five times and vacuum drying was applied to obtain 95.2 g of 1-ethyl-3-methyl imidazolium bis(fluorosulfonyl) imide. As a result of ICP analysis, 3.3 ppm of total alkali metals, 3.1 ppm of chlorine and 5.1 ppm of iodine were contained.

(5) Synthesis of diethyl hexyl methyl ammonium bis(pentafluoroethane sulfonyl)imide (represented by the following compound)

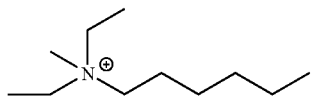 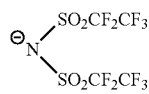

Example 5

To a 200 ml four necked flask equipped with a stirrer, a dropping funnel, a cooling tube and a thermometer, 78.65 g (0.5 mol) of diethyl hexyl amine and 50 ml of methanol were charged and heated, to which 70.04 g (0.50 mol) of trimethyl phosphoric acid was dropped slowly taking one hour or more and refluxed for 15 hours. After reaction, they were cooled to room temperature and 136.80 g of diethyl hexyl methyl ammonium phosphate was obtained by drying under a reduced pressure. Then, 136.80 g of the obtained diethyl hexyl methyl ammonium phosphate was dissolved in 50 ml of water, and a solution in which 189.66 g of lithium bis(pentafluoroethane sulfonyl) imide was dissolved in 50 ml of water was added thereto at a room temperature and stirred. From separated two layers, the lower layer was fractionated and by-products were removed by adding 40 wt % of purified water and water washing five times, and vacuum drying was applied to obtain 262.43 g of diethyl hexyl methyl ammonium bis(trifluoromethane sulfonyl) imide. As a result of ICP analysis, the total alkali metals was 2.4 ppm or less, chloride ion was 0.6 ppm, and each of iodide and bromide ions was 0.1 ppm or less (lower than ICP detection limit).

(6) Synthesis of 1-ethyl-3-methyl imidazolium bis(pentafluoroethyl sulfonyl)imide (represented by the following compound)

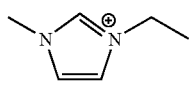 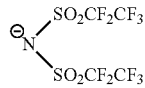

Example 6

To a 200 ml four necked flask equipped with a stirrer, a dropping funnel, a cooling tube and a thermometer, 48.07 g (0.5 mol) of 1-ethyl imidazole and 50 ml of toluene were charged and heated to 100° C., to which 55.07 g (0.50 mol) of methylmethane sulfonic acid was dropped slowly taking one hour or more and reacted for 25 hours. After reaction, they were cooled to room temperature and 101.07 g of 1-ethyl-3-methyl imidazolium methyl sulfonate was obtained by drying under a reduced pressure. Then, 101.07 g of the obtained diethyl hexyl methyl ammonium phosphate was dissolved in 50 ml of water, and a solution in which 189.68 g of lithium bis(pentafluoroethyl sulfonyl)imide was dissolved in 50 ml of water was added thereto at a room temperature and stirred. From separated two layers, the lower layer was fractionated and by-products were removed by adding 40 wt % of purified water and water washing five times, and vacuum drying was applied to obtain 228.71 g of 1-ethyl-3-methyl imidazolium bis(pentafluoromethane sulfonyl)imide. As a result of ICP analysis, the total alkali metals was 1.7 ppm, chloride ion was 0.6 ppm, and each of iodide and bromide ions was 0.1 ppm or less (lower than ICP detection limit).

(7) Synthesis of 1-allyl-1-methyl pyrrolidinium hexafluoro phosphate (represented by the following compound)

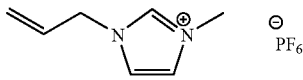 

Example 7

To a 200 ml four necked flask equipped with a stirrer, a dropping funnel, a cooling tube and a thermometer, 54.07 g (0.5 mol) of 1-allyl imidazole and 50 ml of toluene were charged, to which 63.01 g (0.50 mol) of dimethyl sulfuric acid was dropped slowly taking one hour or more and reacted for 5 hours. After reaction, 114.79 g of 1-allyl-3-methyl imidazolium methyl sulfonate was obtained by drying under a reduced pressure. Then, 114.79 g of the obtained 1-allyl-3-methyl imidazolium methyl sulfonate was dissolved in 80 ml of water, and a solution in which 74.44 g of lithium hexafluoro phosphate was dissolved in 80 ml of water was added thereto at a room temperature and stirred. From separated two layers, the lower layer was fractionated and by-products were removed by adding 40 wt % of purified water and water washing five times, and vacuum drying was applied to obtain 127.37 g of 1-allyl-3-methyl imidazolium hexafluoro phosphate. As a result of ICP analysis, the total alkali metals was 2.1 ppm, chloride ion was 0.4 ppm, and each of iodide and bromide ions was 0.1 ppm or less (lower than ICP detection limit).

(8) Synthesis of 1-methyl-3-propyl piperidinium bis(fluoro sulfonyl)imide (represented by the following compound)

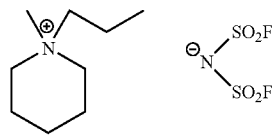 

Example 8

To a 50 ml four necked flask equipped with a stirrer, a dropping funnel, a cooling tube and a thermometer, 4.96 g (0.05 mol) of 1-methyl piperidine and 5 ml of toluene were charged, after heating to 50° C., 10.02 g (0.055 mol) of dipropyl sulfuric acid was dropped slowly taking one hour or more. After reacting for 10 hours, 13.37 g of 1-methyl-3-propyl piperidinium propyl sulfate was obtained by drying under a reduced pressure. Then, 13.37 g of the obtained 1-methyl-3-propyl piperidinium propyl sulfate was dissolved in 8 ml of water, and a solution in which 10.5 g of potassium bis(fluorosulfonyl)imide was dissolved in 8 ml of water was added thereto at a room temperature and stirred. From separated two layers, the lower layer was fractionated and by-products were removed by adding 40 wt % of purified water and water washing five times, and vacuum drying was applied to obtain 15.31 g of 1-methyl-3-propyl pyrrolinium bis(fluorosulfonyl) imide. As a result of ICP analysis, the total alkali metals was 1.8 ppm, chloride ion was 0.5 ppm, and each of iodide and bromide ions was 0.1 ppm or less (lower than ICP detection limit).

(9) Synthesis of tributyl methyl phosphinium bis(trifluoro methane sulfonyl)imide (represented by the following compound)

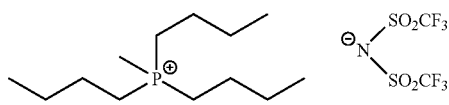

Example 9

To a 50 ml four necked flask equipped with a stirrer, a dropping funnel, a cooling tube and a thermometer, 101.16 g (0.5 mol) of tributyl phosphine and 50 ml of toluene were charged, and 63.07 g (0.05 mol) of dimethyl sulfuric acid was dropped slowly taking one hour or more. After reaction and solvent cleaning with toluene, 159.30 g of tributyl methyl phosphinium methyl sulfate was obtained by drying under a reduced pressure. Then, 159.30 g of the obtained tributyl methyl phosphinium methyl sulfate was dissolved in 80 ml of water, and a solution in which 139.24 g of lithium bis(trifluoromethane sulfonyl) imide was dissolved in 80 ml of water was added thereto at a room temperature and stirred. From separated two layers, the lower layer was fractionated and by-products were removed by adding 40 wt % of purified water and water washing five times, and vacuum drying was applied to obtain 422.88 g of tributyl methyl phosphinium bis(trifluoromethane sulfonyl) imide. As a result of ICP analysis, the total alkali metals was 1.6 ppm, chloride ion was 0.5 ppm, and each of iodide and bromide ions was 0.1 ppm or less (lower than ICP detection limit).

What is claimed is:

1. An ionic liquid, represented by the formula $K^+A^-$, comprising a cation, $K^+$, that is 1-ethyl-3-methyl imidazolium and an anion, $A^-$, that is a halogenated sulfonyl imide anion represented by $[XSO_2]_2N$, X representing halogen, wherein the content of an alkali metal as an impurity in the ionic liquid is 5 ppm or less and the content of a halogen ion is 1 ppm or less.

2. An ionic liquid according to claim 1, wherein the cation is obtained by quarternizing 1-methyl imadazole by using an acid ester represented by the following general formula, $C_2H_5OY$, and then conducting salt exchange, wherein the group OY is selected from the group consisting of:

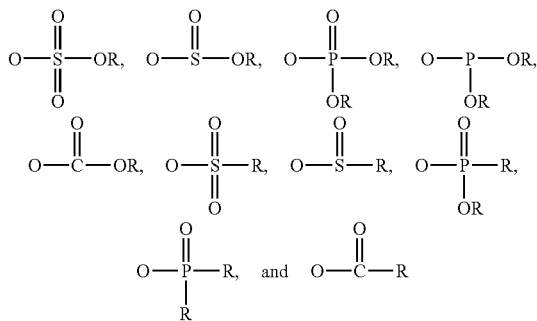

(3)

in which R in the general formula (3) is a linear or branched alkyl group of 1 to 8 carbon atoms and a plurality of R contained in one compound may be identical or different with each other.

* * * * *